US012234603B2

(12) United States Patent
Casad, Jr.

(10) Patent No.: US 12,234,603 B2
(45) Date of Patent: Feb. 25, 2025

(54) HIGH SOLIDS ALKALINE OXIDATION AND BIOMETHANE CONVERSION OF RESIDUAL LIGNIN

(71) Applicant: Robert C. Casad, Jr., Copenhagen (DK)

(72) Inventor: Robert C. Casad, Jr., Copenhagen (DK)

( * ) Notice: Subject to any disclaimer, the term of this patent is extended or adjusted under 35 U.S.C. 154(b) by 42 days.

(21) Appl. No.: 17/907,814

(22) PCT Filed: Mar. 3, 2021

(86) PCT No.: PCT/US2021/020567
§ 371 (c)(1),
(2) Date: Aug. 29, 2022

(87) PCT Pub. No.: WO2021/178468
PCT Pub. Date: Sep. 10, 2021

(65) Prior Publication Data
US 2023/0132267 A1   Apr. 27, 2023

Related U.S. Application Data

(60) Provisional application No. 62/984,302, filed on Mar. 3, 2020.

(51) Int. Cl.
*D21C 11/00* (2006.01)
*C07G 1/00* (2011.01)
*C12P 5/02* (2006.01)

(52) U.S. Cl.
CPC ............ *D21C 11/0042* (2013.01); *C07G 1/00* (2013.01); *C12P 5/023* (2013.01); *D21C 11/0007* (2013.01); *D21C 11/0057* (2013.01)

(58) Field of Classification Search
CPC .. C07G 1/00; D21C 11/0057; D21C 11/0007; D21C 11/0042
See application file for complete search history.

(56) References Cited

U.S. PATENT DOCUMENTS 3,910,873 A * 10/1975 Lin ........................... C08H 6/00
516/47
4,075,248 A * 2/1978 Marshall ................. C07C 45/78
568/438

(Continued)

OTHER PUBLICATIONS

Lyu et al., Alkaline oxidative cracking for effective depolymerization of biorefining lignin to mono-aromatic compounds and organic acids with molecular oxygen, 2018, Biomass and Bioenergy, 108, p. 7-14. (Year: 2018).*

(Continued)

*Primary Examiner* — Anthony Calandra

(57) ABSTRACT

Residual lignin recovered from biological conversion processes and pulp and paper industry wastes can be converted to water-soluble products by alkaline oxidation under oxygen pressure at high solids loading within the temperature range 130-180° C. No problems associated with repolymerization reactions are encountered at solids loading between 10-30% where the initial molar ratio of hydroxide base to lignin residual is at last 0.4, possibly because of enhanced reactivity in the oxidation reaction of aromatic groups in self-associate structures. The water-soluble oxidation products can be fractionated to recover a low molecular weight fraction in which pH can be adjusted using CO2 without forming precipitates. Sodium carbonate byproduct can be recovered from the pH adjusted reaction mixture using acetone precipitation. The low molecular weight fraction of the pH adjusted oxidation products can be used as feed for anaerobic digestion to biomethane.

16 Claims, 7 Drawing Sheets

Size exclusion HPLC elution profile of Indulin AT before (A) and after (B) high solids oxidation as monitored by RI and A280.

(56) References Cited

U.S. PATENT DOCUMENTS

| | | | | | |
|---|---|---|---|---|---|
| 4,151,207 | A | * | 4/1979 | Evju | C08H 6/00 |
| | | | | | 568/432 |
| 4,713,185 | A | * | 12/1987 | Howard | C09K 8/885 |
| | | | | | 166/275 |
| 2011/0297340 | A1 | * | 12/2011 | Kouisni | D21C 11/0007 |
| | | | | | 162/16 |
| 2019/0390405 | A1 | * | 12/2019 | Geigle | D21C 11/0007 |
| 2020/0148835 | A1 | * | 5/2020 | Paleologou | C08H 6/00 |

OTHER PUBLICATIONS

Abdelaziz, O. et al. Abdelaziz, O. et al. "Oxidative Depolymerization of Kraft Lignin for Microbial Conversion." ACS Sustainable Chem. Eng. (2019) 7:11640-11652.

Casimiro, F. et al. Casmiro, F. et al. "Kinetics o f Oxidative Degrada-tion of Lignin-Based Phenolic Compounds in Batch Reactor," Ind. Eng. Chem. Res. (2019) 58:16442.

Deng, H. et al. "Rules and Mechanism for the Oxidation of Lignin-based Aromatic Aldehyde under Alkaline Wet Oxygen," BioResources (2020) 15(2):3487.

Hosoya, T. et al. Hosova. T. et al. "Selective production of bio-based aromatics by aerobic oxidation of native softwood lignin in tetrabutvlammonium hydroxide" RSC Adv (2020) 10:19199.

Li, Y. et al. Li, Y. et al. "Preparation of Syringaldehyde from Lignin by Catalytic Oxidation of Perovskite-Type Oxides," ACS Omega (2020) 5:2107.

Luo, K. et al. "Oxidative conversion of lignin isolated from wheat straw into aromatic compound catalyzed by NaOH and NaALO2," Food Sci. Nutr. (2020) 8:3504.

Lyu, G. et al. "Alkaline oxidative cracking for effective depolymerization of biorefining lignin to mono aromatic compounds and organic acids with molecular oxygen," Biomass and Bioenergy (2018) 108:7-14.

Matheiu Y. et al. "Molecular Oxygen Lignin Denolvmerzation: An Insight into the Stability of Phe-nolic Monomers." Chem. Sus. Chem. (2020) 13:1.

Paananen H. et al. "Base-catalyzed oxidative depolymerization of softwood kraft lignin." Crops and Products (2020) 152:112473.

Rawat S. et al. "Molybdenum-catalyzed oxidative depolymerization of alkali lignin: Selective production of Vanillin," Applied Catalvsis A General (ZU20) 398: 117567.

Schutyser W. et al. "Revisiting alkaline aerobic lionin oxidation" Green Chem. (2018) 20:3828.

* cited by examiner

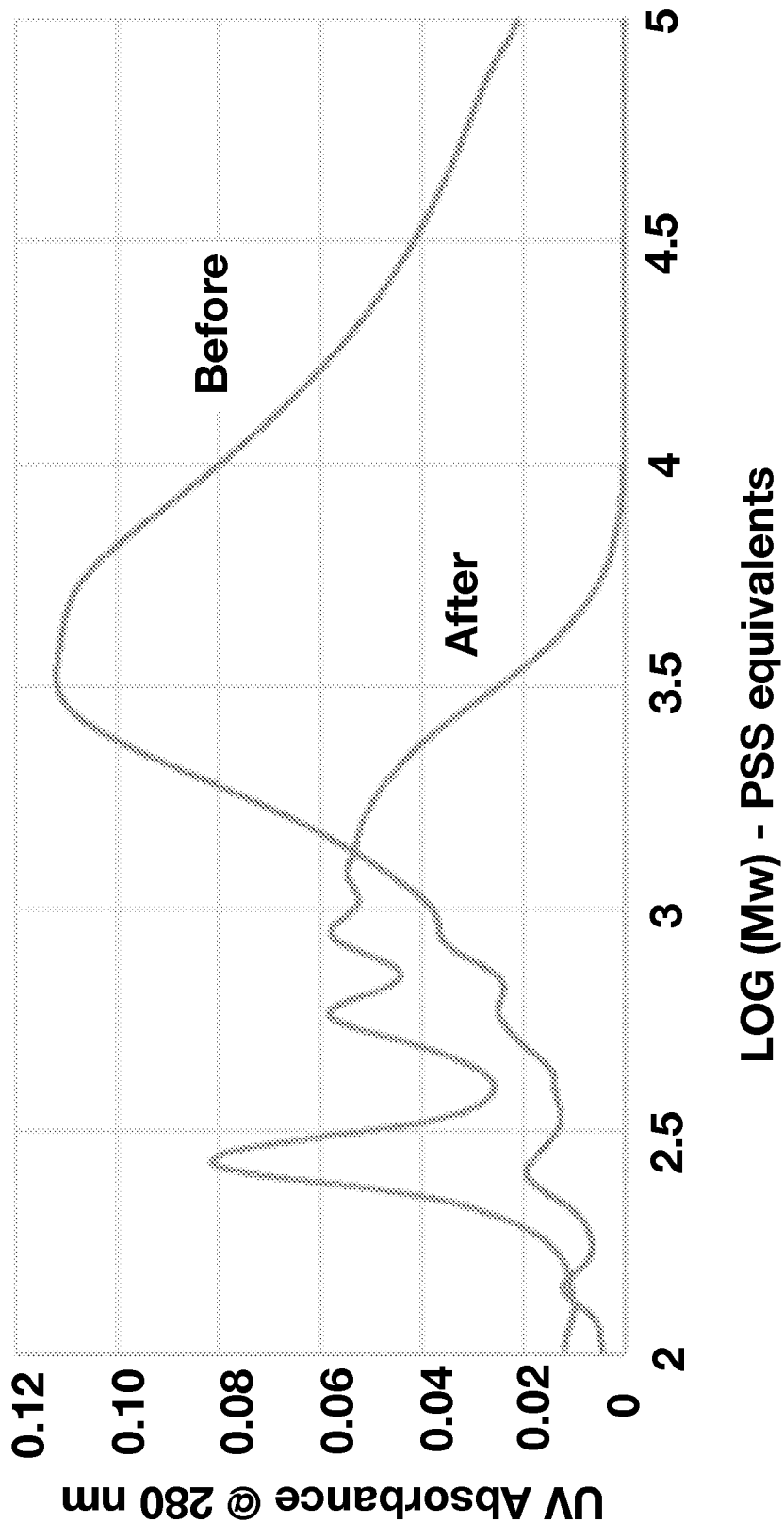
Figure 1. Size exclusion HPLC elution profile of wheat straw lignin before and after high solids alkaline oxidation, as monitored by 280 nm absorbance.

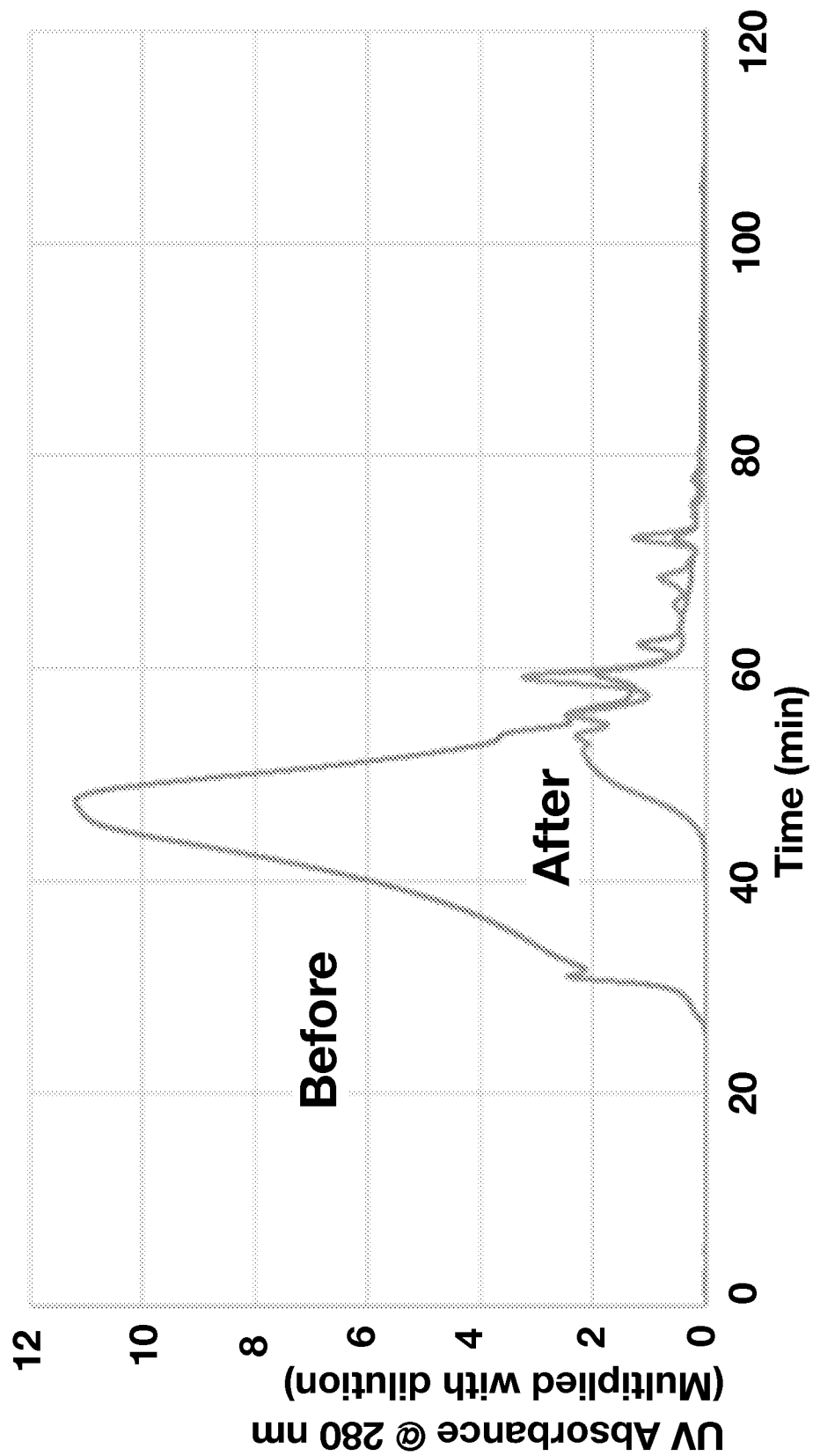
Figure 2. Semi-quantitative comparison of size exclusion HPLC profile of wheat straw lignin before and after high solids oxidation monitored by 280 nm absorbance.

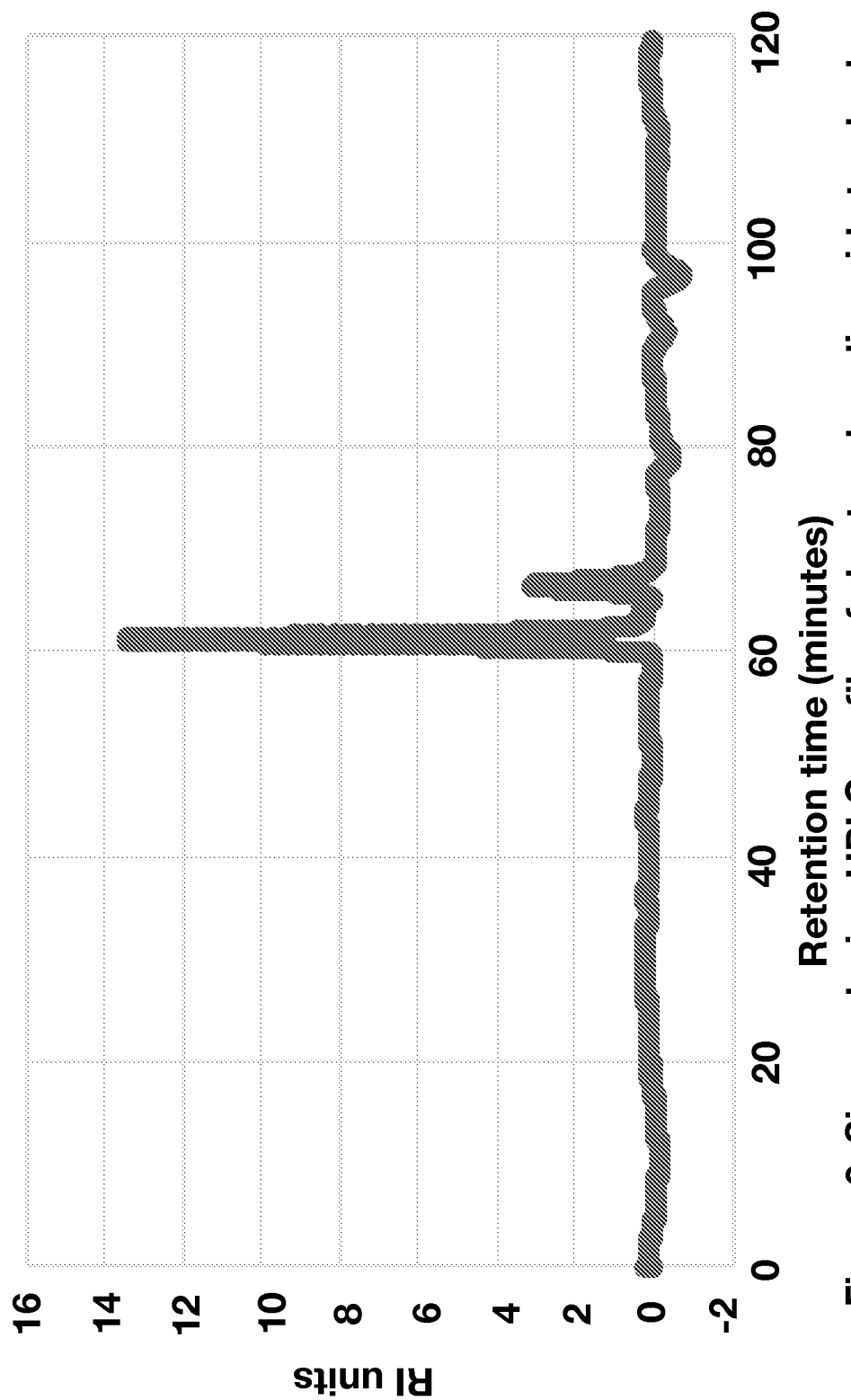
Figure 3. Size exclusion HPLC profile of short carboxylic acid standards.

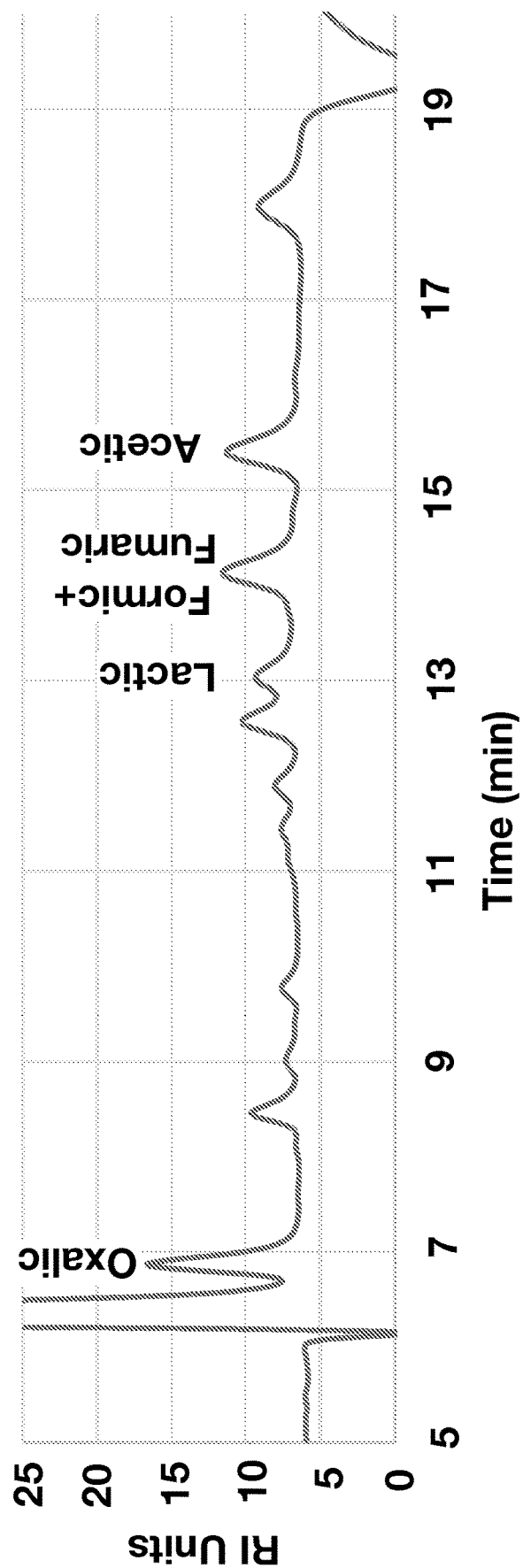
Figure 4. Carboxylic acid HPLC elution profile monitored by RI of wheat straw lignin high solids oxidation products.

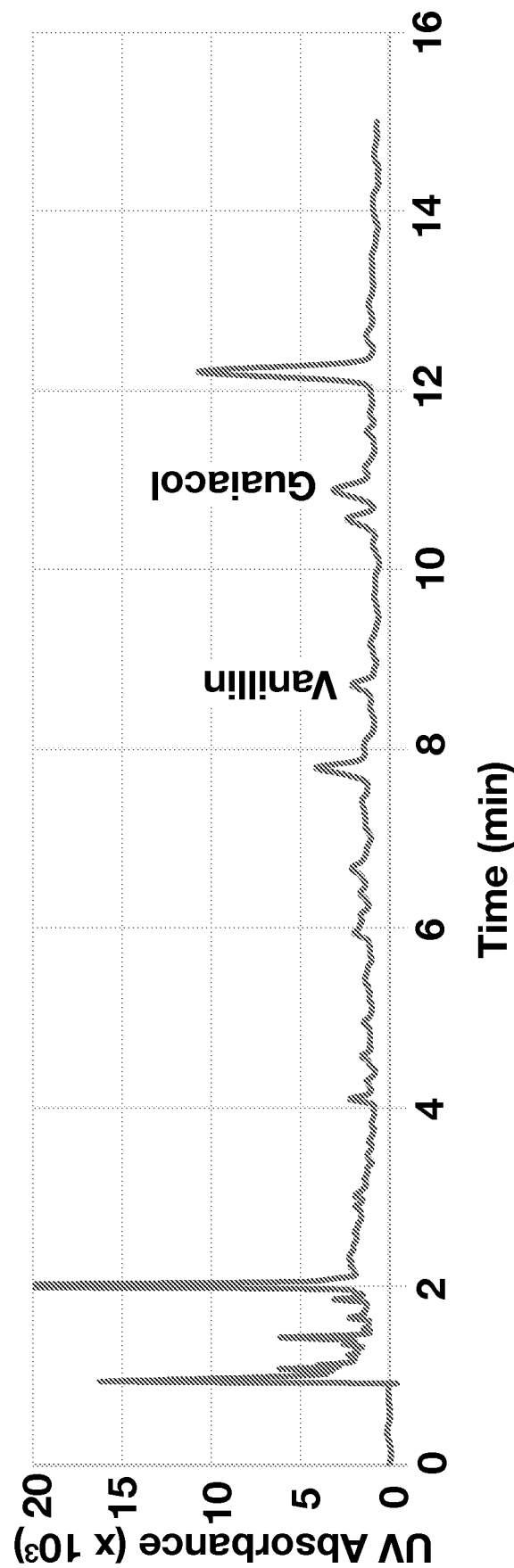
Figure 5. Monoaromatics elution profile of wheat straw lignin high solids oxidation products as monitored by absorbance at 280 nm.

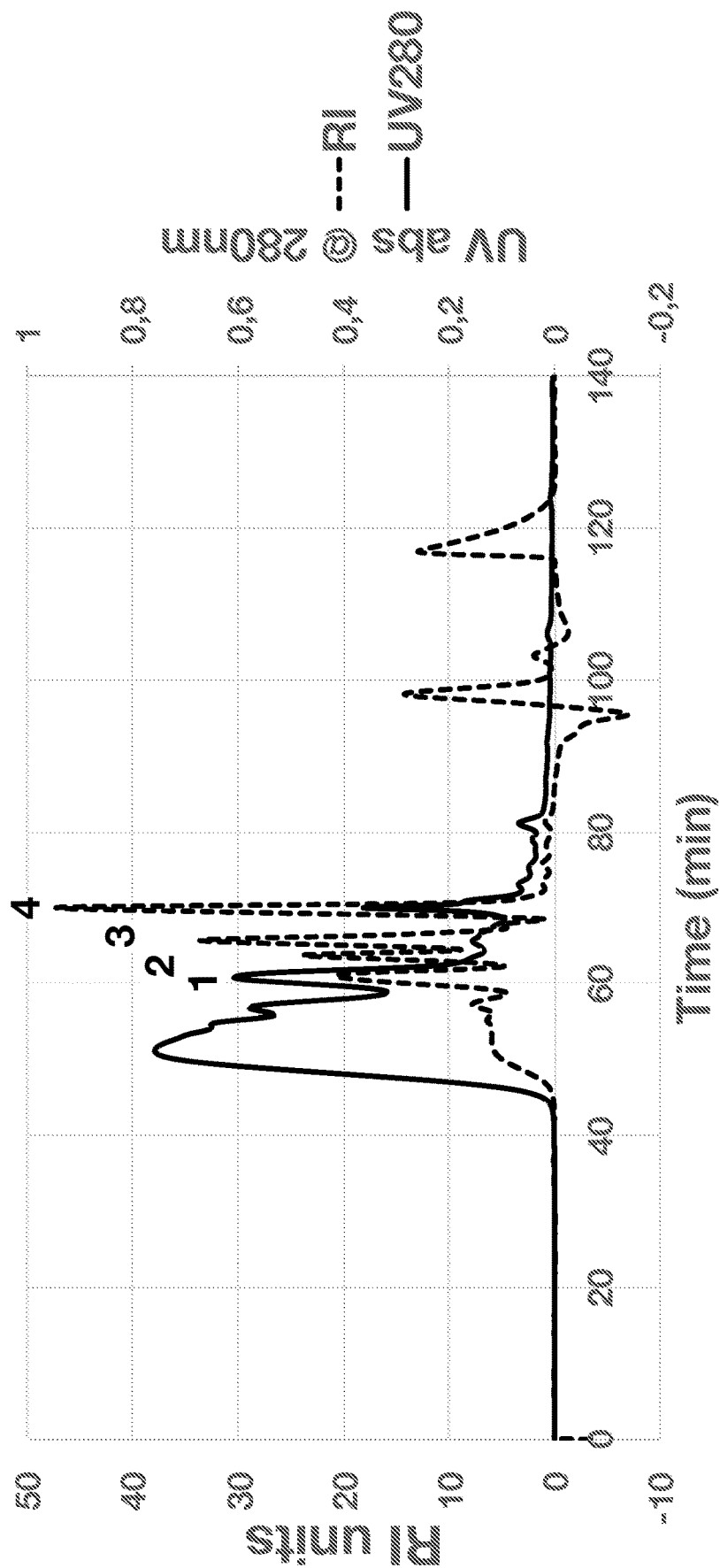
Figure 6. Size exclusion HPLC elution profile of wheat straw lignin high-solids alkaline oxidation products as monitored by RI and A280.

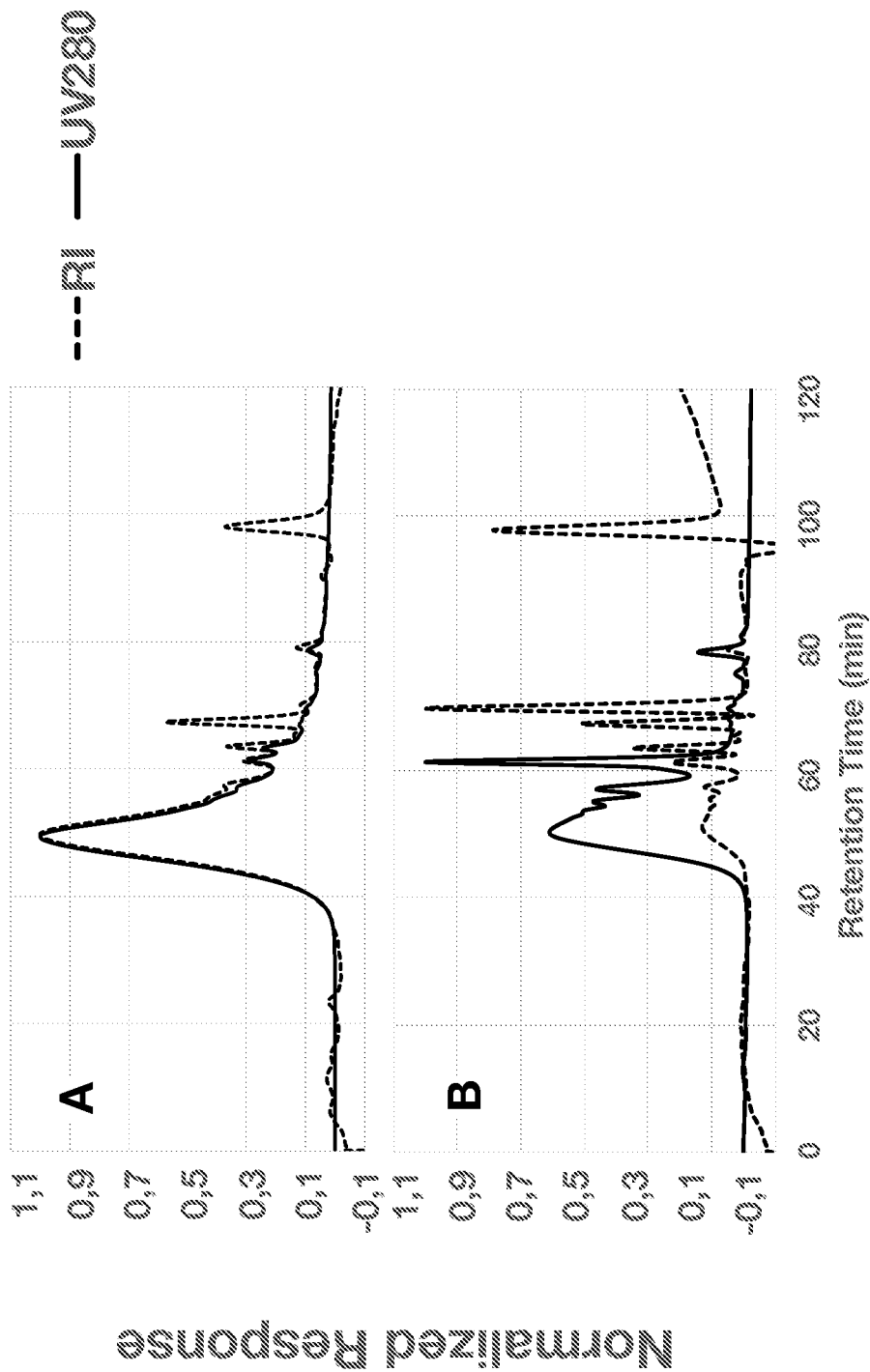
Figure 7. Size exclusion HPLC elution profile of Indulin AT before (A) and after (B) high solids oxidation as monitored by RI and A280.

HIGH SOLIDS ALKALINE OXIDATION AND BIOMETHANE CONVERSION OF RESIDUAL LIGNIN

FIELD

The invention relates generally to biological systems and methods for biomass conversion and in particular to systems and methods that produce a lignin-rich process residual and to methods and devices for oxidative conversion of recovered lignin-rich process residual and in particular to systems and methods that produce biomethane.

Conversion of lignocellulosic biomass to fuels, chemicals and other useful products is widely regarded as critical for development of a sustainable political economic order.

Biogas conversion technologies are particularly promising. Upgraded biomethane can alternatively be stored in a gas grid or used as a universal chemical precursor or as vehicle (or other) fuel while raw biogas can be used for dispatchable electrical power generation during peak demand.

Both thermal and biological gasification technologies are known in the art for biomethane conversion of lignocellulosic biomass. Thermal gasification plants are technically complex, require staffing by highly educated personnel, and can only be commercially practicable on huge scale >30 tons/hour. See e.g. Thunman (2018). In contrast, biological gasification relies on simple fermentation schemes. Anaerobic digestion plants can be commercially practicable on a smaller, de-centralized scale with lower feedstock supply demands (ca 4 tons/hour) and much lower capital and operating costs such as might be appealing for municipal governments and small scale investors.

As shown in Table 1, biological gasification to biomethane is far more efficient in recovering inherent combustion energy of lignocellusic feedstocks as vehicle fuel than any microbial fermentation to liquid fuels such as ethanol, butanol and biodiesel. Yet biological gasification has previously been applied primarily only to low or negative cost substrates while higher cost lignocellulosic feedstocks have been used primarily for less efficient, more expensive liquid biofuel fermentation processes.

We have previously reported simple and commercially practicable processes for recovery of comparatively pure (ca 80%) lignin process residual from biological conversion of steam pretreated lignocellulosic feedstocks (WO2020/033633) and ruminant manure (PCT/US20/62763).

By valorizing this lignin-rich residual, biological gasification of lignocellulosic feedstocks can become commercially attractive.

One possible approach to valorization of recovered lignin-rich residual is that it can be further digested to provide additional methane yield. While native, high molecular weight polymeric lignin is primarily indigestible in conventional anaerobic digestion, it can be chemically oxidized to digestible, water soluble products. Base catalysed lignin depolymerization is well known in the art, whereby lignin is dissolved in hydroxide base solution and then subject to thermal treatment at high temperatures, to break lignin down into monomeric components. The same reaction is termed "alkaline oxidation" when conducted in the presence of added oxidant, such as applied oxygen pressure, typically within the range 130-200° C. The prior art has applied alkaline oxidation to lignin with the aim of recovering very high value chemical products from the reaction product mixture. Depending on reaction conditions, products of the lignin alkaline oxidation reaction can be obtained ranging from lightly oxidized aromatic monomers to extensively oxidized carboxylic acids. Previously, alkaline oxidation of lignin-rich residual has been limited to comparatively low solids loading. At loading >4 wt. %, re-polymerization processes (typically leading to char formation) have proved troublesome under previously tested conditions. See e.g. Demesa (2015) and Mathieu (2020). Prior art studies with alkaline oxidation of lignin and lignin model compounds with applied oxygen pressure have been conducted at solids loading <8%, Paananen (2020), or no greater than 4%, Lyu (2018), Schutyser (2018), Abdelaziz (2019), Casimiro (2019), Deng (2020), Hosoya (2020), Li (2020), Luo (2020), Mathieu (2020), Rawat (2020).

Where the end product is only biomethane, alkaline oxidation of residual lignin can never be commercially practicable in the low solids regime applied in the prior art. But we have discovered that, very surprisingly, alkaline oxidation of lignin can be conducted at very high solids loading >10 wt. % with minimal complications from repolymerization/char formation. With sufficiently high NaOH concentration, we typically see recovery of water-soluble oxidation products from alkaline oxidation at 25 wt. % solids corresponding to >80% of the initial lignin dry matter (DM) content. While the reasons for our success with alkaline oxidation at high solids loading remain the subject of speculation, one contributing factor could be the difference in lignin self-associate structures in low and high solids conditions. Small angle X-ray scattering studies of NaOH solution with 2% lignin derived from soda pulping of sugar cane bagasse identified self-associate structures having radius of gyration 2.3 nm and fractal dimension 2.47. See Maziero (2012). This corresponds to a spherical particle having molecular weight about 25,000, i.e., considerably larger than a typical lignin polymer. Similar studies at 12%, much less 25%, solids have not been reported, but it is reasonable to expect that any self-association tendencies observed at 2% loading will be amplified at higher solids content. Inter-molecular distances are reduced in self-associate structures such that these might promote n-n stacking interactions between lignin aromatic moities which in turn might enhance their reactivity in alkaline oxidation. Very possibly, at high solids loading, lignin is so effectively oxidized that the remaining, fragmented oxidation products are not susceptible of repolymerization.

The possibility to conduct alkaline oxidation of lignin residual at very high solids loading enables commercially practicable application of a "Lignogas™" lignin conversion process in anaerobic digestion. We estimate that, with 70% recovery of lignin content, and 80% conversion to digestible, water soluble products, net methane yields can be increased on the order of 50 $Nm^3$/ton initial feedstock DM. Because it is highly exothermic, when the lignin oxidation reaction is conducted at high loading it becomes a net provider of heat for other plant processes. By "harnessing" the excess heat from alkaline oxidation at high lignin loading, sufficient process heat is obtained to substantially evaporate water content from residual solids remaining after lignin recovery. It can also be advantageous to subject dried residual solids to a thermal gasification process that can "pay" for steam pretreatment cost, while leaving about 50% of carbon content as char. By increasing methane yields while reducing costs for digestate disposal, the business case for biomethane conversion of lignocellulosic wastes can become quite attractive in favorable biomethane markets. This will enable widespread commercial conversion of these abundant feedstocks—a universally applicable approach to rapid expansion of the renewable energy system.

The technology of high solids alkaline oxidation described here can be productively applied to lignin residual from lignocellulosic feedstocks, in general, including straws, energy grasses, forestry residues and wood chips. It can further be productively applied to provide metabolic substrates for other biological conversion systems than biological gasification, including ethanol production and other microbial fermentation schemes. One skilled in the art will also readily recognize that high solids alkaline oxidation of lignin to provide digestible biomethane substrates can be attractive also in the pulp and paper industry and other areas.

TABLE 1

Energy conversion rate and GHG reduction of wheat straw biomass conversion to different microbial biofuels in comparison with LIGNOGAS (™) expected values.

| Fuel fermentation product | Energy conversion efficiency % | GJ fuel theoretical yield/ton DM | GHG reduction ton CO2 equivalent/ ton DM |
|---|---|---|---|
| Butanol theoretical [a] | 41.3 | 8.09 | — |
| Ethanol theoretical [a, e] | 42.3 | 8.29 | 0.66 |
| Ethyl-hexadecanoate [a] theoretical | 38.4 | 7.53 | — |
| Farnescene theoretical [a] | 32.9 | 6.44 | — |
| Biomethane theoretical [b, f] | 95.8 | 18.77 | 1.44 |
| Biomethane actual [c, f] | 53.8 | 10.54 | 0.81 |
| Biomethane LIGNOGAS [d, f] | 64.0 | 12.52 | 0.96 |

All values based on theoretical combustion heat in the feedstock of 19.6 GJ/ton straw.
 a. assumes complete conversion of all 5 and 6 carbon sugars according to the theoretical yields on glucose reported by Rude (2009);
 b. calculated theoretical methane potential of wheat straw 472 Nm$^3$/ton DM based on the average of two values for elemental analysis of whole wheat straw reported by Perez (2015) and Niu (2016);
 c. measured biomethane yield 265 Nm$^3$/ton DM from continuous digestion in a 0.08 m$^3$ reactor as described in WO2020/033633 of wheat straw pellets steam pretreated without agitation;
 d. based on expected biomethane yield from biogas digestion of steam pretreated wheat straw pellets with additional LIGNOGAS conversion technology;
 e. ethanol from straw reduces GHG emissions 85% corresponding to 80 gram CO2-eq./MJ ethanol per EU renewable energy directive (EU-RED);
 f. based on the EU-RED Lantz (2018) calculate that biomethane from straw reduces GHG emissions 82% using state-of-the-art processes.

BRIEF DESCRIPTION OF THE DRAWINGS

FIG. 1. Size exclusion HPLC elution profile of wheat straw lignin before and after high solids alkaline oxidation, as monitored by 280 nm absorbance.

FIG. 2. Semi-quantitative comparison of size exclusion HPLC profile of wheat straw lignin before and after high solids oxidation monitored by 280 nm absorbance.

FIG. 3. Size exclusion HPLC profile of short carboxylic acid standards as monitored by RI.

FIG. 4. Carboxylic acid HPLC elution profile monitored by RI of wheat straw lignin high solids oxidation products.

FIG. 5. Monoaromatics elution profile of wheat straw lignin high solids oxidation products as monitored by absorbance at 280 nm.

FIG. 6. Size exclusion HPLC elution profile of wheat straw lignin high solids oxidation products as monitored by RI and A280.

FIG. 7. Size exclusion HPLC elution profile of Indulin AT lignin before and after high solids alkaline oxidation, as monitored by RI and 280 nm absorbance.

DESCRIPTION OF EMBODIMENTS

In some embodiments, the invention provides a method of processing lignin-rich process residual comprising the steps of:
 providing a solution of at least 10 wt. % lignin-rich process residual dry matter dissolved in an aqueous solution of NaOH, KOH or other strong hydroxide base having pH at least 12 and molar ratio of hydroxide base:lignin residual at least 0.4; and
 subjecting the solution to alkaline oxidation at temperature >100° C. under applied oxygen pressure at least 3 bar for residence time sufficient to yield products that are water soluble at pH 7 comprising at least 50 wt. % of the amount of lignin residual dry matter dissolved in the solution before oxidation.

As used herein, the following terms have the following meanings:

"Alkaline oxidation" refers to a process for conversion of lignin in an aqueous solution of hydroxide base in the presence of applied oxygen pressure as oxidant. Oxygen may be applied as partial pressure in atmospheric air or other gaseous mixture.

"Applied oxygen pressure" refers to oxygen partial pressure delivered to an oxidation reaction mixture during all or part of its residence time at a temperature >100° C.

"Ash content" refers to material remaining in a sample after heating to 550° C. for 6 hours.

"Biological conversion process" refers to a microbiological process for transforming lignocellulosic biomass into usable products. The term includes but is not limited to enzymatic saccharification, fermentation for production of specific products, and anaerobic digestion for production of biomethane.

"Hydrothermal pretreatment" refers to the use of water either as hot liquid, pressurized steam, or both to "cook" biomass at temperatures within the range 130-210° C.

"Lignin-rich process residual" refers to lignin dry matter content remaining as residual after some method of processing ruminant manure and/or lignocellulosic biomass. The lignin residual, recovered in a mixture of residual materials, is "lignin-rich" to the extent that Klason lignin content of the non-ash content of the mixture is at least 60 wt. %, where ash, carbohydrate and lignin content are determined from dried samples as described in "Determination of structural carbohydrates and lignin in biomass," Laboratory Analytical Procedure issue date April 2008 US National Renewable Energy Laboratory Technical Report NREL/TP-510-42618 revised August 2012, except that all calculations are made without correction for extractives and except that acid soluble lignin content is determined using 205 nm absorptivity of 110 L/g cm and except that equivalent reagents and laboratory equipment to that specifically named by brand may be used.

"Molar ratio of hydroxide base:lignin residual" refers to the molar ratio of hydroxide base in aqueous solution to the molar ratio of lignin rich process residual (non-ash content) calculated assuming that the process residual has molecular weight 180 corresponding to a theoretical lignin "monomer," regardless of its composition (i.e., lignin purity).

The amount of "products that are water soluble at pH 7" is determined by adjusting the oxidation products to pH 7, if necessary. Whatever form the pH adjusted oxidation products may take, they are then centrifuged at 3800 g for 30 minutes, water-soluble supernatants decanted, and "pellets" of whatever form resuspended in 4 volumes of neutral water and re-centrifuged. The process of serial dilution of centrifuge pellets is repeated until no change in pellet size is observed. The supernatants from serial dilution are filtered using MUNKTELL™ microglass fiber filters and any filter cake mass quantified by drying at 105° C. Drying at 105° C. leads to an underestimate of water-soluble DM content because some of the material is volatile and follows water evaporation, typically including at least acetic acid, formic acid and guaiacol. The final pellet DM is quantified by drying at 105° C. followed by heating at 550° C. for 6 hours to determine ash content. The measured ash content is applied to the filter cake DM to estimate its non-ash content. To the extent that the combined weight of the final pellet non-ash DM and any filter cake non-ash DM comprises <50 wt. % of the initial amount of lignin residual dry matter dissolved in the solution before oxidation, products that are water soluble at pH 7 are deemed to comprise at least 50 wt. % of the amount of lignin residual dry matter dissolved in the solution before oxidation. As used herein the term "water soluble" can be applied to material that forms micelle-like structures giving rise to much higher apparent solubility in this measurement than the intrinsic solubility of a monomeric form of the material might suggest.

"Weight %" in a solution is the percentage that a component comprises of the total weight of the solution, including solvents and other solutes.

Suitable lignin-rich process residual may be derived from a variety of sources including but not limited to Kraft lignin from pulp and paper industry processing, or undigested lignin content from anaerobic digestion of ruminant animal manure or from anaerobic digestion or other fermentation of steam pretreated lignocellulosic feedstocks. In some embodiments, lignin-rich residual is recovered from a biological conversion process, optionally using any of the methods described in WO2020/033633 or PCT/US20/62763, each of which is hereby expressly incorporated by reference in entirety. In some embodiments, Kraft black liquor concentrated by ultrafiltration processes is directly used as the lignin-rich process residual in high solids alkaline oxidation.

In some embodiments, the methods of high solids alkaline oxidation of the invention are applied to at least 11 g of lignin-rich process residual, or at least 200 g, or at least 1 kg, or at least 10 kg, or at least 100 kg. In some embodiments the method is practiced as a continuous process.

Alkaline oxidation of lignin-rich process residual can normally be conducted at solids loading above 4 wt. % with reasonable yields where the initial conditions are at pH at least 13 with a molar hydroxide base:lignin residual loading at least 0.8. In some embodiments, loading of lignin-rich process residual dry matter in the alkaline oxidation reaction is at least 5 wt. %, or at least 7, or at least 10, at least 12, or between 7 and 30, or greater than 15. In some embodiments, initial hydroxide base:lignin residual molar ratio is at least 0.4, or 0.5, or 0.8, or 0.9, or 1.0, or between 0.8 and 1.3, or between 1.0 and 1.5. In some embodiments, yield expressed as weight percentage of initial dry matter (DM) loading rendered water soluble at pH 7 by the oxidation reaction is at least 50 wt. %, or at least 60, or at least 70, or between 50 and 99.9%. In some embodiments, initial conditions in the alkaline oxidation reaction are at pH at least 12. The high solids alkaline oxidation can be conducted such that the reaction mixture has some residence time at temperature within the range 110-200° C. or advantageously within the range 130-180° C. Residence times at temperature within these ranges can be within the range 5 to 120 minutes but is advantageously within the range 15 to 60 minutes. The high solids alkaline oxidation reaction is typically continuously stirred. While sodium hydroxide and potassium hydroxide can be used with the least process complexity, other strong hydroxide bases such as LiOH produced from disposal of spent batteries can also be used.

Oxygen partial pressure can be applied by means well known in the art using compressed air, in which the oxygen content is typically about 20-22 vol. %, or using an oxygen generator, in which oxygen content of air is enriched. In some embodiments, oxygen partial pressure during alkaline oxidation is applied using an oxygen generator which enriches oxygen content of air to >50 vol. %, or >60 vol. %, or >70 vol. %, or >80 vol. %. In some embodiments, applied oxygen partial pressure is at least 2 bar, or at least 3 bar, or at least 5 bar, or at least 7 bar, or at least 10 bar, or at least 12 bar, or between 5 and 20 bar, or between 2 and 20 bar. In some embodiments, oxygen partial pressure is applied during heat up and the first half of residence time at temperature within the range 110-200° C., but then stopped to permit complete consumption of oxygen in the reactor head space. In some embodiments, oxygen partial pressure is applied for the entire residence time at temperature within the range 110-200° C., but then stopped during a cool down and holding period.

The high solids alkaline oxidation converts water-insoluble, high molecular weight lignin into a mixture of water-soluble, low molecular weight products that can, in theory, be readily converted to biomethane in a subsequent biological process. This high solids reaction of the invention is without precedent in the prior art literature. Thus, our results do not necessarily "map" onto previous work with alkaline oxidation at much lower solids loading.

The primary component of the products from high solids alkaline oxidation of lignin within the temperature range 130-180° C. under conditions where at least 3 bar oxygen pressure was applied is carboxylic acids. The oxidation reaction is invariably associated with a loss of 280 nm absorbance associated with aromatic ring structures. Loss of 280 nm absorbance in alkaline oxidation has previously been shown to correspond to ring-opening reactions. See Maziero (2012). As is apparent in FIG. 2, which is explained in Example 2, >80% of the 280 nm absorbance of wheat straw lignin recovered from anaerobic digestion was lost during oxidation at 25 wt. % solids in 1.3 M KOH with 15 bar oxygen pressure. The figure 80% is almost certainly an underestimate of the loss of aromatic groups where extinction coefficients per g short-chain lignin oligomers are known to be much greater by a factor on the order of 7× compared with high molecular weight lignin. See e.g. Lim (2018).

The chemical mechanisms of aromatic ring-opening in alkaline oxidation of lignin has been studied in some detail in the context of oxygen bleaching of Kraft pulp, typically at lignin solids loading about 1% and at temperatures on the order 110° C. The basic mechanism for oxygen-induced aromatic ring-opening was presented by Gierer (1997). Phenolic rings are cleaved leaving two carboxylic acid ends in the reaction product. In the case of monomeric model compounds, Suzuki (2006) directly showed that H2O2 oxidation cleaves the aromatic group into a dicarboxylic acid (muconic) which can further degrade into smaller acids.

Asgari and Argyropoulos (1998) documented the time course of carboxylic acid formation and showed that these could occur either as short acids or as functional groups on larger fragments. Rovio (2011) clearly documented formation of carboxylic acid moieties on lignin fragments, i.e. ring-opening conversion to dicarboxylic acid ends on high molecular weight lignin polymers.

The introduction of carboxylic acid groups renders short lignin oligomers to be, themselves, water soluble. Such short, water-soluble oligomers derived from a much milder treatment at 200° C. for 1 hour with no added oxygen were previously shown to be converted by an anaerobic consortium to CH4 and CO2. Colberg and Young (1982). These soluble oligomers were then isolated and used as sole carbon source for anaerobic cultures. Shorter oligomers were more readily converted. Colberg and Young (1985a). In the specific case of a water soluble 600 MW lignin-derived oligomer, digestion to aromatic monomers was documented. Colberg and Young (1985b). In theory, aromatic ring metabolism, while metabolically complex, can be achieved in perfect conditions in anaerobic digestion with nearly 100% theoretical yields. Healy and Young (1979).

The oxidation reaction introduces a considerable amount of oxygen content into the reaction products. For example, 1 kg of lignin converted with perfect efficiency to aliphatic carboxylic acids will produce between 1.5 to 1.8 kg of product DM. Even where the mixture of oxidation products includes a significant percentage of compounds with low biomethane potential, such as oxalic acid and formic acid, the overall theoretical biomethane potential of the product mixture in the theoretical case of perfect conversion to carboxylic acids typically corresponds to between 59-73% of the theoretical potential of the initial lignin content.

The products of high solids alkaline oxidation of lignin typically include some short, water soluble lignin oligomers, a mixture of carboxylic acids, and some mono-aromatic acids and other compounds. As explained above, short, water-soluble lignin oligomers are indeed digestible. A mixture of short-chain carboxylic acids can typically be digested in a matter of hours with nearly 100% theoretical methane yields. See e.g. Dinsdale (2000). However, realization of this inherent methane potential can require some "finesse" because the mono-aromatic components are well known to inhibit biomethanation. See e.g., Monlau (2014).

In some embodiments, the lignin oxidation product is used, either as a process stream in a continuous process or as a batch output, as feed for anaerobic digestion to produce additional biomethane. In some embodiments, it may be advantageous to feed the oxidation products at high pH as a source of alkalinity in a digestion with acidic feeds. In some embodiments, it may be advantageous to adjust pH of the oxidation products to a range typically suitable for biogas digestion between 7 and 8.5.

In some embodiments, lignin oxidation products are subject to a fractionation method that separates low molecular weight components from higher molecular weight components. Any convenient method of fractionation known in the art can be applied including but not limited to ultrafiltration using tubular ceramic or polymeric membranes as described by Arkell (2014) and Li (2019) with Kraft black liquor. Typically an ultrafiltration system with 1 kilodalton (kD) molecular weight cut-off is ideal for fractionation of high solids lignin oxidation products. In some embodiments, a membrane having 2 kD molecular weight cutoff may be used, or a membrane within the range 600 to 2000 MW. Where pH of the oxidation reaction products is adjusted after separation of high molecular weight components >1 kD, little to no precipitation is observed. In contrast, where pH of the unfractionated oxidation reaction products is reduced, the mixture typically forms a "gooey" or "spongey" semi-solid mass. Water soluble components still typically comprise most of the reaction products, but these become "trapped" in this semi-solid mass. It is possible to recover the water-soluble products through serial dilution of this semi-solid mass. But as a practical matter, it is advantageous to handle an undiluted liquid for further processing. In some embodiments, using the fraction of components of the lignin oxidation products <1 kD, pH can be conveniently adjusted using CO2, which is in abundant supply at biogas plants. The use of CO2 for pH adjustment of the alkaline oxidation products leads to accumulation of carbonate within the reaction mixture, as described by Salmon (2018). CO2 formed during the oxidation reaction is also expected to accumulate in solution as carbonate. In some embodiments, the hydroxide base used for alkaline oxidation is sodium hydroxide or potassium hydroxide. Either sodium or potassium carbonate formed during pH adjustment can be recovered as a process byproduct by acetone precipitation as described by Ellingboe (1966) by adding acetone to the mixture sufficient to make a final weight % acetone >25 in the solution. In some embodiments, acetone is added to a pH-adjusted fraction of components of the lignin oxidation products <1 kD, or <2 kD, to a wt. % within the range 25-45%. In some embodiments, the acetone/water mixture is filtered to recover sodium or potassium carbonate. Acetone solvent can then be easily recovered for re-use by means well known in the art. While potassium hydroxide is invariably more expensive than sodium hydroxide, potassium carbonate is much more valuable as a byproduct than sodium carbonate and can advantageously be used as fertilizer notwithstanding some contaminants in the recovered product. Sodium or potassium carbonate solutions are themselves well known to capture CO2 such that administration of CO2 in an amount that exceeds that required to reach the desired pH can be advantageously applied as a means of increasing sodium or potassium carbonate byproduct yields.

In some embodiments, anaerobic digestion of lignin alkaline oxidation products is conducted using a secondary digestion system separate from the primary digester. In some embodiments, this separate secondary digester is an upflow anaerobic sludge blanket (UASB) reactor or any form of fixed biofilm digestion system known in the art. Fixed film systems are generally less susceptible to inhibitors than ordinary continuous stirred tank reactors (CSTRs). See for example the digestion of toxic aqueous fraction from hydrothermal liquefaction of biomass reported in Si (2018). In some embodiments, anaerobic digestion of lignin alkaline oxidation products is conducted using a fixed orientation, fixed biofilm anaerobic digestion system adapted to provide a laminar "plug flow" of liquid feed subject to continuous re-circulation such as the systems described by Escudie (2011) and by WO2016/050893, which is hereby expressly incorporated by reference in entirety. Similar systems have been used to digest feed streams rich in aromatic acids, e.g. Escudie (2011) (wine vinasse) and Arreola-Vargas (2018) (tequila vinasse). These systems proved robust to aromatic acids levels up to at least 1.5 g/L. The upper limit of aromatic acid tolerance in such a system was never determined because this question did not previously arise.

Such fixed orientation, fixed biofilm systems are advantageous because they permit a laminar flow in which only a small portion of the feed is in contact with the biofilm at any given time. Gas output provides a small amount of turbulent mixing at the biofilm/feed stream interface. A concentration gradient is established across the biofilm for substrates that are actively consumed. However, for inhibitors, which are typically not consumed, no concentration gradient across the biofilm is established. The implication is that such a system can be run at whatever may be the limiting concentration of inhibitor, while rapidly consuming the easily digested aliphatic carboxylic acids. Residence times in such a system can be literally a matter of only hours when running at low organic loading, i.e., at some limiting inhibitor concentration.

One skilled in the art can readily determine, without undue experimentation, appropriate residence time at predetermined reaction temperature which is sufficient to yield products that are water soluble at pH 7 comprising at least 50 wt. % of the amount of lignin residual dry matter dissolved in the solution before oxidation. The % conversion to water soluble DM can be determined as explained in the definitions above.

In some embodiments, the process is further characterized in that excess process heat produced by the alkaline oxidation reaction is recovered by means known in the art and applied towards other processes at a biogas plant. The precise stoichiometry of lignin alkaline oxidation will vary with reaction conditions and lignin properties. Net production of process heat can be seen in a generalized theoretical example as follows:

C10H12O3+4O2+3H2→1succinic+2 acetic+1 glycolic 23.3-25.6 MJ/kg lignin combustion heat=4.1-4.5 MJ/mol

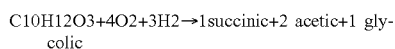

Theoretical loss in this case is between 0.17 and 0.57 MJ/mol (between 4.1 and 12.6%)→between 1.03 and 3.16 MJ/kg→between 1030 and 3160 MJ/ton lignin.

In some embodiments, excess process heat is applied to dry solid residual remaining after lignin recovery from anaerobic digestion of steam pretreated lignocellulosic feedstocks or from some other biological conversion process. Lignin recovery can be by methods described in WO2020/033633 or by other methods known in the art. In some embodiments, solid process residual, optionally partially dried using excess process heat from the lignin oxidation reaction, is used as feedstock for a gasification system that produces additional process heat via a combustible hot gaseous product. In some embodiments, the gasification system comprises both a pyrolysis reactor and a separate char reactor, such as the PYRONEER™ system described in Thomsen (2017). In some embodiments, the gasification process is intentionally conducted so as to maximize char carbon recovery while providing process heat for other plant processes, such as using the process described by Zhang (2018). In some embodiments, hot product gas from gasification is directly combusted in a steam boiler to provide heat for steam pretreatment, and/or to provide heat for CO2 gasification of residual char. In some embodiments, gasification of residual char is conducted using CO2 (which is plentiful at biogas plants), for example, as described by any of Lahijani (2015), Kirtania (2016), Wang (2016), Hu (2019) or Zhang (2019). In some embodiments, CO-rich syngas produced by CO2 gasification of residual char having low H2:CO molar ratio <1 is further subject to a catalytic conversion process such as described by Andersson (2015) to produce a mixture of gaseous and liquid products which are usable in a biomethane conversion plant. The gaseous products are hydrocarbon gases such as methane, ethane and propane which will not negatively affect biogas upgrading. The liquid products are a mixture of alcohols such as methanol, ethanol, propanol and butanol, and other oxygenates, such as methyl formate, each of which is readily convertible to biomethane in anaerobic digestion. In some embodiments, the entire product stream from catalytic conversion of CO-rich syngas can be directly transferred to the same separate, secondary anaerobic digestion system used to process lignin alkaline oxidation products, and thereby fed into the plant's overall biogas upgrading system. In some embodiments, CO-rich syngas is converted to the biomethane substrate acetic acid using a co-culture biological process such as that described by Lee (2018). In some embodiments, the CO-rich syngas product from residual char gasification can be directly fed into a biomethane reactor adapted to consume CO and H2 as described by Henstra (2011), Diender (2015) and Diender (2018).

In some embodiments, the invention provides a process for biological conversion of lignocellulosic feedstocks comprising the steps of:
  providing lignocellulosic biomass feedstock,
  hydrothermally pretreating the lignocellulosic feedstock at temperature within the range 130-210° C.;
  using the pretreated feedstock as biomass input to a biological conversion process,
  recovering lignin-rich process residual from the biological conversion process as a solution in hydroxide base having at least 7 wt % lignin-rich residual dry matter (DM),
  subjecting the lignin hydroxide solution to alkaline oxidation at a temperature >100° C. under applied oxygen pressure at least 3 bar for residence time sufficient to yield products that are water soluble at pH 7 comprising at least 50 wt. % of the amount of lignin residual dry matter dissolved in the lignin hydroxide solution before oxidation; and
  valorizing the resulting alkaline oxidation products.

A suitable biological conversion process may be anaerobic digestion to produce biomethane or enzymatic hydrolysis to produce fermentable sugars to be used in some fermentation process or any process known in the art. In some embodiments, the biological conversion process may be anaerobic digestion of a mixture of substrates, for example including manure, to which steam pretreated lignocellulosic feedstocks are added as a supplement. Any suitable lignocellulosic biomass may be used, including but not limited to any combination of straw feedstocks including wheat, barley, rice, oat, rye, canola, rape, rice and corn straw (including stover), wood chips, sawdust, or other paper or lumber production wastes, energy grasses such as *Miscanthus*, switchgrass, reed canary grass, giant reed grass, wild native prairie grass or other feedstocks. Hydrothermal pretreatment can be conducted according to any suitable method known in the art. In general, pretreatment can be advantageously conducted in such manner as to avoid agitation of the feedstock during pretreatment, as described in WO2020/0033633 and in WO2018/085487, which is hereby expressly incorporated by reference in entirety. One skilled in the art will, without undue experimentation, readily arrive at appropriate conditions for hydrothermal pretreatment for the biological conversion system of interest. Recovery of lignin-rich process residual as an aqueous solution in hydroxide base can be achieved using any of a variety of means known in the art, including but not limited to means disclosed in WO2020/033633 and PCT/US20/62763. In some embodiments, lignin alkaline oxidation products are valorized by anaerobic digestion to biomethane.

In some embodiments, the invention provides a system for biological conversion of lignocellulosic feedstocks comprising:
- a primary anaerobic digestion biomethane reactor or a primary saccharification reactor,
- means for recovering lignin content of digestate from the biomethane reactor or saccharification reactor as an aqueous solution in strong hydroxide base,
- a lignin oxidation reactor equipped to process the lignin hydroxide solution at temperatures >100° C. under applied oxygen pressure at least 3 bar, and
- means for producing oxygen or pressurized air sufficient to provide applied oxygen partial pressure at least 3 bar.

In some embodiments, the lignin oxidation reactor may be a continuous reactor.

In some embodiments, the system may further comprise:
- a steam boiler, a steam pretreatment reactor for pretreatment of lignocellulosic feedstocks and means for feeding pretreated biomass into the primary biomethane reactor; and/or
- means for recovering reaction heat from the lignin oxidation reactor and applying it to another plant process; and/or
- a secondary anaerobic digestion reactor separate from the primary anaerobic digestion reactor or saccharification reactor fitted with communication means to receive oxidation products from the lignin oxidation reactor; and/or
- a primary gasification reactor with ancillary equipment adapted to dry and gasify solid process residual fitted with communication means to transmit gaseous product to a steam boiler; and/or
- a secondary char gasification reactor adapted to provide $CO_2$ gasification of char residual from the primary gasification reactor; and/or
- communication means for delivery of a $CO_2$ stream from biogas upgrading either to the gasification reactor or to a secondary char gasification reactor; optionally further including
- a syngas catalytic conversion reactor fitted with communication means to transmit products to an anaerobic digestion reactor.

Any or all of the steam pretreatment, lignin oxidation or gasification reactors can be continuous reactors.

It will be readily understood by one skilled in the art that features of the various embodiments can be combined. For example, in alkaline oxidation, any initial pH condition may be combined with any hydroxide base:lignin residual molar ratio and any applied oxygen pressure. Or for example, a system for biological conversion may be configured to practice any steam pretreatment, alkaline oxidation, gasification or syngas conversion conditions using any lignin rich process residual.

EXAMPLES

1. High Solids Alkaline Oxidation at 15 Bar Applied Oxygen Pressure of Wheat Straw Lignin Recovered from Anaerobic Digestate A lignin-rich process residue recovered previously was used for experiments. The sample was recovered from digestate of homogeneous biogas digestion of steam pretreated wheat straw pellets as described in WO2020/033633, example 17. The sample had 25% by weight dry matter (DM) content of lignin-rich process residual dissolved in 7.3% KOH (1.3 M). The non-ash content of the lignin-rich material comprised approximately 79% Klason lignin, 4% carbohydrate and 17% non-carbohydrate impurity, primarily comprising wax. Taking molecular weight of lignin "monomer" as 180, and applying this figure to the entire contents of the residual, the KOH:lignin molar ratio was 0.935. The pH of the sample before oxidation was 13.68.

An aliquot of 47.62 g of this sample was poured into a 100 ml Parr reactor fitted with a charging device effective to deliver gas at constant pressure. The reactor was then sealed and heated under 15 bar applied oxygen partial pressure while vigorously stirring, applying constant pressure in the high solids reaction similar to the initial pressurization conditions reported by Lyu (2018) in low solids loading. The sample was heated to 160° C. over a period of 30 minutes. During the course of heating, it became apparent that reaction heat from the exothermic oxidation of lignin was contributing to the heating process. The total pressure when the reactor reached 157° C., as measure, was 35 bar, which is approximately 12 bar higher than expected. The reactor temperature as measured reached 164° before dropping to 161° C., at which point the pressure was 28 bar, which was still higher than expected. The temperature was maintained at 161° C. for 30 minutes, after which the reactor was surrounded with an ice water bath for rapid cooling.

After the reactor reached room temperature, it was unsealed and the sample decanted. Some char-like material was accumulated on the sides of the reactor and on the stirring apparatus. This was removed by washing in acetone, and the acetone-recovered dry matter was subsequently quantified. The decanted sample post-oxidation had pH 10.40. The pH was adjusted to 6.95 by addition of small aliquots of 18 M HCl. The pH was adjusted again to 6.95 after the sample was diluted with 40 ml of water. The net dilution vol/vol of the sample counting pH adjustment and added water was 2 final:1 initial. The sample was then centrifuged at 3983 g for 30 minutes in two 50 ml conical tubes. The supernatant was decanted then filtered using MUNKTELL™ micro-glass fiber filter paper without binder. Dry matter retained by the filter was determined by drying at 105° C.

The pellets from the original centrifugation of the sample were washed in water (pH 7.0) then centrifuged again at 3893 g for 30 minutes. The supernatants were decanted and also filtered using MUNKTELL™ micro-glass fiber filter paper. The process of washing the pellets and filtering the resulting supernatants was repeated an additional three times for 4 washes in all. Dry matter remaining in the centrifuge pellets after 4 wash steps was determined by drying at 45° C.

Solubilization of DM during the oxidation reaction was estimated to be 78.9%: Initial DM added (other than KOH ash content) was 11.905 g. Char recovered in acetone was 0.55 g or 4.6%. DM retained by filters was 1.814 g or 15.2%. DM remaining in the final centrifuge pellet was 0.156 g or 1.3%. DM remaining in filtrate was thus estimated to be an amount corresponding to 78.9% of the lignin residual DM dissolved before oxidation. This is considered to be a reasonable approximation of the degree of solubilization at pH 7.

These results are consistent with effectively 99.6% of lignin content having been solubilized during alkaline oxidation, where the wax content of the NaOH solubilized dry matter used would not be expected to be reactive.

This shows that the exothermic alkaline oxidation of lignin residual from biogas digestate can be conducted at much higher DM levels than have previously been reported.

2. Analysis of Wheat Straw Lignin Oxidation Products

A sample of centrifuged and filtered oxidation products from the supernatant of the original centrifugation described in example 1 was filtered again using a 0.2 um HPLC preparation filter. Samples for HPLC characterization of carboxylic acid content were made from dilutions of this sample. For molecular weight determination, samples were diluted in 0.1 M NaOH. For carboxylic acid characterizations, samples were diluted in 5 mM $H_2SO_4$. The net dilution of the oxidation products, including dilution during sample preparation described in example 1, used in the HPLC samples was 40:1. A 1:100 dilution of the initial sample before alkaline oxidation was used for comparison by size exclusion HPLC.

The size exclusion elution profile of the sample before and after alkaline oxidation, as monitored by 280 nm absorbance is shown in FIG. 1. The HPLC-system used Superdex™ 200 Increase and Superdex™ 30 Increase column in series. Mobile phase was 0.1 M NaOH at a flow rate of 0.5 ml/min. Molecular weight equivalents were determined based on comparison with the elution of PSS™ molecular weight standards. As shown, the sample was well depolymerized by alkaline oxidation. The remaining lignin content can be crudely estimated as follows: The amount of "theoretical lignin equivalent" in the "after" sample was 2.5× the amount used in "before." The molar extinction coefficient at 280 nm of short chain lignin oligomers is greater than that of long chain lignin oligomers by a factor on the order of 7×. See Lim (2018) table 2; compare entry 6 and 7. By assuming that the short chain oligomers (<1000 MW) have 7× the extinction coefficient of long chain oligomers (>1000 MW), and that the area under the A280 curve is linearly proportional to mass, these results are consistent with the interpretation that approximately 7% of the lignin content remained in oligomeric form after alkaline oxidation. The remaining 93% of lignin content appears to have been converted to a combination of aliphatic and aromatic carboxylic acids, possibly with some lignin monomers and short oligomers having varying degrees of carboxylation. FIG. 2 shows the raw A280 signal multiplied by the sample dilution to show a semi-quantitative alignment of the "before" and "after" samples. The integrated A280 area under the elution profile curve for the "after" sample in FIG. 2 was 19.8% of the integrated value for the "before" sample. As shown, most of the A280 content has disappeared from the sample, consistent with conversion of lignin to aliphatic carboxylic acids. The results plainly show >80% conversion, but this is almost certainly an underestimate, where molar extinction coefficient at 280 nm is much greater for the short-chain and monomeric lignin-derived products with residual aromatic groups.

FIG. 3 shows the RI size exclusion elution profile in this HPLC system of a standard of short chain carboxylic acids comprising 8 mg methyl malonic acid, 4.4 mg succinic acid and 1.9 mg glyceric acid in 3.6 ml of 0.1 M NaOH. Each of these acids was identified as a product of lignin alkaline oxidation as reported by Lyu (2018). As shown, these acids clearly interact with the column matrix giving rise to an elution position that misrepresents their actual molecular weight. For example, the main peak at 61 minutes corresponds to an apparent molecular weight of about 1000.

The elution profile of the oxidation products on an Aminex HPX-87H column from BIO-RAD™ for the analysis of organic acids (mobile phase 5 mM $H_2SO_4$, flow rate 0.6 ml/min) as monitored by refractive index (RI) is shown in FIG. 4. Standard curves with 5 dilutions between 10 g/L and 0.1 g/L were run concurrently with the oxidation sample for lactic, acetic, oxalic, and formic acids. Standards were not available at the time of this HPLC run for the other carboxylic acid products identified by Lyu (2018) in alkaline oxidation of lignin—glycolic, glyceric, maleic, malonic, succinic, methylmalonic and methylsuccinic acids. As shown, there is an abundance of carboxylic acids in the oxidation products. Peaks that could be identified are labeled. In this elution, formic and fumaric acids could not be distinguished. Calculated concentrations were lactic 2.3 g/L, acetic 3.7 g/L, oxalic 2.2 g/L, fumaric/formic 1.8 g/L.

The elution profile of the wheat straw lignin oxidation products on a Waters BEH C18 column used for analysis of monoaromatics including lignin monomers, as monitored by absorbance at 280 nm, is shown in FIG. 5. Only vanillin and guaiacol could be definitely identified. Early eluting peaks appear to include a significant amount of monoaromatic acids.

Both the normalized RI and normalized A280 elution profiles of the wheat straw lignin oxidation products in size exclusion HPLC as described above are shown in FIG. 6. The peak labeled 1 is present in significant amounts as shown by the RI trace and also has significant 280 nm absorbance. This is believed to correspond to short lignin oligomers, possibly carboxylated by aromatic ring-opening reactions. The peaks labeled 2, 3 and 4 having little or no 280 nm absorbance are believed to correspond primarily to carboxylic acids. The small peaks between 75 and 85 minutes are believed to correspond to monoaromatic acids. The large peaks between 95 and 125 minutes are salt peaks. However, in light of the observed interactions of carboxylic acids with the column matrix, which give rise to anomalous apparent molecular weights, the second, late eluting salt peak could also be non-salt material that experiences column interactions. None of the known salts tested gave rise to a salt peak later than 100 minutes in this elution system.

3. Estimation of Theoretical Methane Potential of Wheat Straw Lignin Oxidation Products As a theoretical example, it is possible to back-calculate the amount of lignin required to produce the observed quantities of known carboxylic acids obtained in example 2, assuming no loss of carbon as $CO_2$, and taking lignin MW as 180, having formula $C_{10}H_{12}O_3$. One example of such a calculation is shown in Table 2.

As shown, in the case of 100% conversion according to this reaction scheme, the yield of carboxylic acid dry matter from lignin dry matter is 1.76×. The theoretical methane potential of the oxidation products can be readily calculated, as shown in Table 3. As shown, in theory through 100% conversion to carboxylic acids, 72% of the inherent lignin methane potential can be realized.

Thus, assuming 73% recovery of lignin with 100% conversion to carboxylic acids, the theoretical net improvement of methane yield over our primary yield from digestion of steam pretreated wheat straw is 67.8 m3/ton DM, or approximately 25.6%.

TABLE 2

Increased dry matter yield from alkaline oxidation.

| Acid and BMP | g/L | Cmol | Hmol | Omol | MW | Mol/L | O acids mol/L | C acids mol/L | H acids mol/L | Lig eq. mol/L | Lig eq. g/L | O Lig g/L | O inc. mol/L | O inc. g/L |
|---|---|---|---|---|---|---|---|---|---|---|---|---|---|---|
| Lactic 373 | 2.2 | 3 | 6 | 3 | 90 | .024 | .073 | .073 | .147 | | | | | |
| Acetic 373 | 3.7 | 2 | 4 | 2 | 60 | .062 | .123 | .123 | .247 | | | | | |
| Oxalic 62 | 2.2 | 2 | 2 | 4 | 90 | .024 | .098 | .049 | .049 | | | | | |
| Fumaric 290 | 1.8 | 4 | 4 | 4 | 116 | .016 | .062 | .062 | .062 | | | | | |
| | | | | | | .126 | .357 | .308 | .504 | .031 | 5.544 | .092 | .264 | 4.228 |

TABLE 3

Theoretical methane potential of lignin oxidation products.

| Acid | g/L | Theoretical methane yield ml/g DM | Theoretical methane yield ml/L oxidation products | Theoretical methane yield ml/L from 5.54 g/L lignin | Realizable methane yield as % lignin theoretical |
|---|---|---|---|---|---|
| lactic | 2.2 | 373 | 820.6 | | |
| acetic | 3.7 | 373 | 1380.1 | | |
| oxalic | 2.2 | 62 | 136.4 | | |
| fumaric | 1.8 | 290 | 522 | | |
| | | TOTAL: | 2859.1 | 3966.64 | 72.079 |

TABLE 4

Example calculation of excess reaction heat from alkaline oxidation of lignin.

| Substance | mol | Combustion heat MJ/mol | Combustion heat MJ | % LOSS |
|---|---|---|---|---|
| Lignin | .031 | 4.5 | 0.140 | 17.935 |
| Lactic acid | .024 | 1.36 | 0.033 | |
| Acetic acid | .062 | 0.88 | 0.055 | |
| Oxalic acid | .024 | 0.25 | 0.006 | |
| Fumaric acid | .016 | 1.33 | 0.021 | |
| | | SUM ACIDS: | 0.114 | |

4. Estimation of Excess Reaction Heat from High Solids Alkaline Oxidation of Lignin At high lignin loading, the alkaline oxidation of lignin is not only autothermal but is a significant net producer of process heat. The loss from the theoretical reaction described in example 3 can be calculated by determining the difference in heats of combustion of lignin and of the carboxylic acids formed from lignin. The calculation is shown in Table 4. As shown, in the case of 100% conversion according to this particular reaction scheme, the excess reaction heat is 17.9% of the combustion heat of lignin. The carboxylic acids produced by the alkaline oxidation reaction will undoubtedly be more widely distributed over all of the acids identified by Lyu (2018). However, the excess reaction heat result should be qualitatively similar to the one shown here.

An experimental estimation of excess reaction heat can be made as follows: Reaction products from high solids alkaline oxidation of lignin-rich can be carefully dried using a rotovap apparatus with condensate collected. Condensate can be analysed for content of volatile components expected to include at least acetic acid, formic acid, guaiacol and possibly other compounds. The estimate of volatile components can be used to correct the dry matter determination of the rotovap concentrate by drying at 105° C. The heat of combustion of the starting material and of the dried oxidation products can then be determined experimentally using a bomb calorimeter. The heats of combustion of the missing volatile components can be estimated from literature values. The difference in heat of combustion between the starting material and the oxidation products provides an estimate of excess reaction heat.

5. High Solids Alkaline Oxidation of Purified Kraft Lignin at 7.8 Bar Applied Oxygen Pressure Indulin AT™ was dissolved in 1.2 M NaOH at a final concentration of 27.9% wt/wt with assumed negligible ash content. The molar hydroxide base:lignin residual loading was thus 1.2/1.55 or 0.77. This solution, having 1.2 liters volume, was subject to alkaline oxidation at 160° C. using a Buchiglas Uster 2.0 liter autoclave which is certified to 60 bar. This system is not fitted with a charging device such that the actual effective partial pressure of oxygen applied is the difference between the nominal pressure supplied by the oxygen tank regulator and the pressure within the reactor. Nominal applied pressure was 14 bar. However, the autologous reactor pressure was 6.2 bar such that, with this apparatus, under these reaction conditions, the effective applied oxygen partial pressure was 7.8 bar. Reaction self-heating is not detectable in this system where the temperature is controlled by cooling water and heating oil. The reaction was conducted with 20 minutes heating to 160° C., 30 minutes at 160° C., 20 minutes cooling to 20° C., and 20 minutes holding at 20° C. Oxygen pressure was initiated when the reaction reached 160° C. and terminated when the cooling sequence began. At the end of the reactor sequence, there was no remaining excess pressure indicating that all oxygen within the head space was consumed during cooling. The pH at the end of the reaction had only dropped to 12.8. Notably, there was no sign of any char whatsoever at the end of the reaction.

The normalized size exclusion HPLC elution profile as monitored by both RI and A280 is shown in FIG. 7 for the Indulin AT™ solution before (A) and after (B) high solids alkaline oxidation. HPLC was conducted as described in example 2. As shown, similar to the results with wheat straw lignin at 15 bar oxygen pressure, most of the material was apparently converted to carboxylic acids with some remaining short lignin oligomers, possibly carboxylated. It is not surprising to see similar results with Kraft lignin at only 7.8 bar oxygen pressure compared with wheat straw lignin at 15 bar—the Kraft process has already substantially depolymerized the lignin. This is apparent in comparison of the wheat straw lignin before oxidation in FIG. 2 with Indulin AT™ before oxidation in FIG. 7.

The pH of the oxidation products was adjusted using HCl. By the time the mixture had reached pH 7, it had a "gooey" consistency. This "goo" was centrifuged at 3800 g for 10 minutes. The resulting supernatants were decanted, the pellet re-suspended in 4× water, and the centrifugation repeated. Through this process of serial washing of the centrifuge pellets 7 times in all, non-ash DM corresponding to 80.0% of the Indulin initially added to the reaction was recovered in a dilute aqueous phase having concentration of volatile solids of 2.24% wt/wt, as determined by drying at 105° C. This is an underestimate, where drying at 105° C. with these products is associated with loss of volatile material. The estimated recovery of water-soluble products thus corresponds to >80 wt. % of the initial lignin DM.

The water-soluble oxidation products mixture was distinctly black in color and had a distinct odor. It is likely that some of these water-soluble oxidation products are forming micelle-like structures such that their apparent solubility is much higher than their actual, inherent solubility.

6. Anaerobic Digestion of Lignin Oxidation Products

The dilute mixture of water-soluble lignin oxidation products referred to in Example 5 was tested in a quick (21 day) biomethane potential test at CELIGNIS laboratories, Limerick, Ireland. The material was plainly shown to inhibit the control digestion.

A 10 liter continuous biogas digester from Bioprocess Control, Lund, Sweden, was converted to a fixed orientation, fixed biofilm reactor patterned after the system described in examples 1 through 5 of WO2016/050893. The reactor was fitted with two pieces of wire mesh in the middle of the tank that define an enclosure for 22 pieces of BioBlok 300™ polyethylene carrier cut to 26 cm length. The stirring shaft was fitted with two stirrers which operate in the volumes both immediately above and immediately below the carrier enclosure. The digester contents were recirculated continuously at the rate 26 liters per hour (turnover time 23 minutes) drawing from the bottom and feeding in through the top using a Watson Marlow model 603S peristaltic pump fitted with tubing having 10 mm internal diameter. The feed into the tank was delivered by a peristaltic pump through a port on the side. The outflow was through an S shaped tube on the side of the digester which provided displacement of a volume equivalent to the feed input. Gas flow from the reactor was routed through an AMPTS 2™ system from BioProcess Control, Lund. The water jacket was connected with a water bath set to 37° C.

The reactor was filled with inoculum obtained from Scandinavian Biogas Fuels AB plant in Södertörn, Sweden. An effort was made to initiate biofilm formation using a "mixed diet" of whey protein used to emulsify safflower oil with table sugar. Ethanol content was included to suppress bacterial growth in the feed tank. This feed was mixed with the dilute water-soluble lignin oxidation products referred to in example 5 such that approximately 9% of total volatile solids was lignin oxidation products. The level 9% was used because at 10% lignin oxidation products, the emulsion began to separate and the feed was unusable. The C:N ratio not accounting for ethanol or lignin oxidation products was approximately 20:1.

The reactor was fed continuously for 7 weeks at a feed rate corresponding to approximately 5 kg VS/m3/day. Robust biogas production was observed with no evidence of inhibition by the lignin oxidation products detected. However, during week 8, the recirculation hose burst and the reactor contents were emptied, ending the experiment.

7. High Solids Alkaline Oxidation of Purified Kraft Lignin at 3.8 Bar Applied Oxygen Pressure Lignoboost lignin from UPM was dissolved in 1.15 M NaOH at a final concentration of 20.4% wt/wt with assumed negligible ash content. The molar hydroxide base:lignin residual loading was thus 1.15/1.13 or 1.02. This solution, having 1.2 liters volume, was subject to alkaline oxidation as described in example 5, except that the nominal applied oxygen pressure was 10 bar, resulting in an effective applied oxygen pressure using this apparatus under these reaction conditions of 3.8 bar. The pH before oxidation was 13.66 while after oxidation it had dropped to 12.24. At the end of the reactor sequence, there was again no remaining excess pressure indicating that all oxygen within the head space was consumed during cooling. There was again no sign of any char whatsoever at the end of the reaction.

8. Molecular Weight Fractionation of Lignin Oxidation Products

The lignin oxidation products referred to in example 8 were subject to ultrafiltration using a Millipore Ultracel PLAC1 kD™ membrane with >1 kD nominal size retention with approximately 14 bar nitrogen pressure. The ultrafiltration cell was filled and a "first pass" low molecular weight permeate was recovered after about 60% volume reduction of the cell contents. The contents were then diluted with water and a "second pass" low molecular weight permeate collected.

It was apparent that a considerable amount of volatile components, presumably including at least formic acid, acetic acid and guaiacol, were lost during drying at 105° C. An estimate of the drying error was based on the assumption that the DM content of the solution after oxidation could not be less than the DM content of lignin initially added. Based on the observed volume reductions and dilutions, 22.6% of the retentate at the end of the "second pass" ultrafiltration comprised a remainder of low molecular weight material present in the original oxidation products. The distribution of DM under these oxidation conditions was thereby estimated to be 51.6%<1 kD (low molecular weight), 48.4%>1 kD (high molecular weight).

9. Adjustment of Lignin Oxidation Products' pH Using CO2

The separation of high molecular weight component of lignin oxidation products referred to in example 9 was repeated a total of 4 times. The "first pass" low molecular weight permeate from each of the 4 ultrafiltration runs was combined. The pH of the combined material was then adjusted using CO2. The regulator output line from a CO2 tank was fitted with a fish tank aerator stone (i.e., sparger) attached by super glue. CO2 pressure was applied through the sparger. The pH dropped from 12.24 to 7.8 in 12 minutes.

A clear titration plateau was observed at pH 9.7 At pH 7.8, the mixture began to produce foam quite "aggressively." Notably pH 7.8 is ideal for biogas digestion. No precipitate was formed. The pH adjusted material was then subject to centrifugation 15 minutes at 3800 g. While no precipitate per se was observed, a diffuse layer of material at the bottom of the centrifuge bottle appeared to be in the process of forming a gel.

10. Recovery of Sodium Carbonate Using Acetone Precipitation

The use of CO2 to adjust pH is expected to result in production of sodium carbonate, which has market value as a byproduct even with impurities. If potassium hydroxide is used in the alkaline oxidation step, recovered potassium carbonate would have much higher market value as a fertilizer, which should be readily usable despite some impurities. Acetone was added to the pH adjusted "first pass" low molecular weight components of lignin oxidation products referred to in example 10 to a final wt. % 42.2. This solution was then stored in a cold room for approximately 8 weeks during a period in which laboratories at Lund University were on lockdown as part of a COVID19 defensive protocol. The acetone/water solution was then filtered. A total of 7.92 g of filtrate DM was recovered, of which 90.7% was ash after 6 hours at 550° C. (mean of N=2).

When this ash was subject to an additional 5 hours at 950° C., the 950° ash as a % of 550° ash was 76.2% (mean of N=2). If the 550° ash had been pure Na2CO3, we would expect the 950° ash to comprise 62%. The ash had an aqua color. When an attempt to dissolve the 950° ash with water was made, the aqua component did dissolve. When this aqueous suspension was centrifuged at 3800 g, the remainder comprised at least two distinctly different white-colored layers in the pellet. While no violent reaction occurred as expected with Na2O, the results are consistent with sodium carbonate having been recovered in a context where contaminating salts reacted with it during the 950° heating. To the extent that this explanation is correct, the observed results are consistent with having recovered 6.0 g of Na2CO3 (having 2.6 g sodium content), along with 1.18 g of other contaminating salts and 0.74 g of organic content. The original sample of filtrate DM was estimated to contain 12.4 g sodium, based on the dilution of the sodium content in the pH-adjusted "first pass" low molecular weight components of lignin oxidation products referred to in example 9. Thus, the presumed sodium carbonate recovery was on the order of 21% of what might theoretically have been achieved. Because sodium carbonate solution itself acts as a means of CO2 capture, sodium carbonate recoveries could likely be improved by continuing to administer CO2 beyond the point where the pH has reached 7.8.

This result was confirmed qualitatively by measurements of inorganic carbon content using a Shimadzu total organic carbon analyzer. A sample of the pH-adjusted "first pass" low molecular weight component of lignin oxidation products from example 9 was diluted appropriately so that the concentration of oxidation products matched the concentration in the acetone-diluted filtrate referred to in this example 10. The absolute value of the inorganic carbon measurements obtained do not seem reliable in that they were suspiciously high. However, it is conceivable that inorganic carbon content was not only that formed during pH adjustment but also included some component accumulated during the oxidation reaction. CO2 produced by the oxidation reaction is expected to accumulate in solution under these conditions, as described by Salmon (2018). In any case, the relative amount of inorganic carbon was reduced in the acetone/water filtrate by a factor of approximately 4.

11. High Solids Alkaline Oxidation of Purified Kraft Lignin at 15.4 Bar Applied Oxygen Pressure Lignoboost lignin from UPM was dissolved in 1.30 M NaOH at a final concentration of 20.5% wt/wt with assumed negligible ash content. The molar hydroxide base:lignin residual loading was thus 1.30/1.14 or 1.14. This solution, having 1.2 liters volume, was subject to alkaline oxidation as described in example 5, except that the oxygen tank was fitted with a new regulator and nominal applied oxygen pressure was 21.5 bar, resulting in an effective applied oxygen pressure using this apparatus under these reaction conditions of 15.4 bar. While the pH before oxidation was 13.93, after oxidation it was 9.95. At the end of the reactor sequence, there was 8 bar remaining pressure. It is unclear whether this represented unused oxygen in the head space or accumulated CO2. At pH >10, any CO2 produced by the oxidation reaction is expected to accumulate in solution under these conditions, as described by Salmon (2018). However, in this case, the pH dropped to a level beneath 10. Thus, the residual pressure could plausibly be from CO2. There was again no sign of any char whatsoever at the end of the reaction.

12. High Solids Alkaline Oxidation of Concentrated Kraft Black Liquor at 15.4 Bar Applied Oxygen Pressure Kraft black liquor concentrated to 22.76% DM as measured by drying at 105° C. was obtained from Sun Carbon AB, Lund, Sweden. Lignin concentration of this material was measured as 203.5 g/L as determined by 280 nm absorbance and an extinction coefficient of 24.6. A solution comprising 13.8 wt. % lignin, 2.4 wt. % unknown DM and 3.7 wt. % added NaOH was prepared using the concentrated black liquor. The molar hydroxide base:lignin residual loading was thus at least 0.76/1.13 or 0.67. This solution, having 1.21 liters volume, was subject to alkaline oxidation as described in example 11. The pH before oxidation was 13.99, after oxidation it was 11.48. At the end of the reactor sequence, there was 9 bar remaining pressure. It is again unclear whether this represented unused oxygen in the head space or accumulated CO2. There was again no sign of any char whatsoever at the end of the reaction.

The embodiments and examples described are exemplative only and not intended to limit the scope of the invention as defined by the claims.

ACKNOWLEDGMENT

The advice and assistance of Prof. Ola Wallberg and the Lund University Department of Chemical Engineering is hereby gratefully acknowledged.

PATENT REFERENCES

WO2020/033633
WO2018/085487
WO2016/050893
PCT/US20/62763

NON-PATENT REFERENCES

Abdelaziz, O. et al. "Oxidative Depolymerization of Kraft Lignin for Microbial Conversion," ACS Sustainable Chem. Eng. (2019) 7:11640-11652

Andersson, R. "Catalytic conversion of syngas to higher alcohols over MoS2-based catalysts," Ph.D. dissertation, 2015, KTH Royal Institute of Technology, School of Chemical Science and Engineering, Department of Chemical Engineering and Technology, Stockholm Sweden.

Arkell, A. et al. "Process performance in lignin separation from softwood black liquor by membrane filtration," Chemical Engineering Research and Design (2014) 92:1792.

Arreola-Vargas, J. et al. "Effect of the organic loading rate on the performance and microbial populations during the anaerobic treatment of tequila vinasses in a pilot-scale packed bed reactor," J Chem Technol Biotechnol (2018) 93: 59.

Asgari, F. and Argyropoulos, D. "Fundamentals of oxygen delignification. Part II. Functional group formation/elimination in residual kraft lignin," Can. J. Chem. (1998) 76:1606.

Casmiro, F. et al. "Kinetics of Oxidative Degradation of Lignin-Based Phenolic Compounds in Batch Reactor," Ind. Eng. Chem. Res. (2019) 58:16442.

Colberg, P. and Young, L. "Biodegradation of lignin-derived molecules under anaerobic conditions," Can. J. Microbiol. (1982) 28:886.

Colberg, P. and Young, L. "Anaerobic Degradation of Soluble Fractions of [14C-Lignin] Lignocellulose," Applied and Environmental Microbiology (1985a) 49(2): 345.

Colberg, P. and Young, L. "Aromatic and Volatile Acid Intermediates Observed during Anaerobic Metabolism of Lignin-Derived Oligomers," Applied and Environmental Microbiology (1985b) 49(2):350.

Dinsdale, R. et al. "Anaerobic digestion of short chain organic acids in an expanded granular sludge bed reactor," Water Research (2000) 34(9):2433.

Demesa, A. et al. "Alkaline Partial Wet Oxidation of Lignin for the Production of Carboxylic Acids," Chem. Eng. Technol. (2015) 38(12):2270-2278.

Deng, H. et al. "Rules and Mechanism for the Oxidation of Lignin-based Aromatic Aldehyde under Alkaline Wet Oxygen," BioResources (2020) 15(2):3487.

Diender, M. et al. "Pathways and Bioenergetics of Anaerobic Carbon Monoxide Fermentation," Frontiers in Microbiology (2015) doi: 10.3389/fmicb.2015.01275.

Diender, M. et al. "High Rate Biomethanation of Carbon Monoxide-Rich Gases via a Thermophilic Synthetic Coculture," ACS Sustainable Chem. Eng. (2018) 6:2169-2176

Ellingboe, J. and Runnels, J. "Solubilities of Sodium Carbonate and Sodium Bicarbonate in Acetone-Water and Methanol-Water Mixtures," Journal of Chemical and Engineering Data (1966) 11(3):323.

Escudie, R. et al. "Control of start-up and operation of anaerobic biofilm reactors: An overview of 15 years of research," Water Research (2011) 45:1-10.

Gierer, J. "Formation and Involvement of Superoxide ($O_2$.—/$HO_2$.) and Hydroxyl (OH.) Radicals in TCP Bleaching Processes: A Review," Holzforschung (1997) 51:34.

Healy, J. and Young, L. "Anaerobic Biodegradation of Eleven Aromatic Compounds to Methane," Applied and Environmental Microbiology (1979) 38:84.

Henstra, A. and Stams, A. "Deep Conversion of Carbon Monoxide to Hydrogen and Formation of Acetate by the Anaerobic Thermophile *Carboxydothermus hydrogenoformans*," International Journal of Microbiology (2011) doi:10.1155/2011/641582

Hosoya, T. et al. "Selective production of bio-based aromatics by aerobic oxidation of native soft wood lignin in tetrabutylammonium hydroxide," RSC Adv. (2020) 10:19199.

Hu, Y. "A Comparison Between CO2 Gasification of Various BiomasasssCChharasrs and Coal Char," Can. J. Chem. Eng. (2019) 97:1326.

Kirtania, K. and Bhattacharya, S. "CO2 gasification behavior of biomass chars in an entrained flow reactor," Biomass Cony. Bioref. (2016) 6:49.

Lahijani, P. et al. "Advances in CO2 gasification reactivity of biomass char through utilization of radio frequency irradiation," Energy (2015) 93:976.

Lantz, M. et al. "Biogas and Ethanol from Wheat Grain or Straw: Is There a Trade-Off between Climate Impact, Avoidance of iLUC and Production Cost?," Energies (2018) 11:2633.

Lee. C. et al. "Co-culture-based biological carbon monoxide conversion by *Citrobacter amalonaticus* Y19 and Sporomusa *ovata* via a reducing-equivalent transfer mediator," Bioresource Technology (2018) 259:128.

Li. K. et al. "Membrane Separation of the Base-Catalyzed Depolymerization of Black Liquor Retentate for Low-Molecular-Mass Compound Production," Membranes (2019) 9:102.

Li, Y. et al. "Preparation of Syringaldehyde from Lignin by Catalytic Oxidation of Perovskite-Type Oxides," ACS Omega (2020) 5:2107.

Lim, J. et al. "Laccase-Catalyzed Synthesis of Low-Molecular-Weight Lignin-Like Oligomers and their Application as UV-Blocking Materials," Chem. Asian J. (2018) 13:284.

Luo, K. "Oxidative conversion of lignin isolated from wheat straw into aromatic compound catalyzed by NaOH and NaALO2," Food Sci. Nutr. (2020) 8:3504.

Lyu, G. et al. "Alkaline oxidative cracking for effective depolymerization of biorefining lignin to mono-aromatic compounds and organic acids with molecular oxygen," Biomass and Bioenergy (2018) 108:7-14.

Mathieu, Y. et al. "Molecular Oxygen Lignin Depolymerization: An Insight into the Stability of Phenolic Monomers," Chem. Sus. Chem. (2020) 13:1.

Maziero, P. et al. "Structural features of lignin obtained at different alkaline oxidation conditions from sugarcane bagasse," Industrial Crops and Products (2012) 35:61.

Monlau, F. et al. "Do furanic and phenolic compounds of lignocellulosic and algae biomass hydrolyzate inhibit anaerobic mixed cultures? A comprehensive review," Biotechnology Advances (2014) 32:934.

Niu, W. et al. "Twenty-two compositional characterizations and theoretical energy potentials of extensively diversified China's crop residues," Energy (2016) 100:238.

Paananen, H. et al. "Base-catalyzed oxidative depolymerization of softwood kraft lignin," Industrial Crops and Products (2020) 152:112473.

Perez, D. et al. "Characterisation of the Most Representative Agricultural and Forestry Biomasses in France for Gasification," Waste Mass Valor. (2015) 6:515.

Rawat, S. et al. "Molybdenum-catalyzed oxidative depolymerization of alkali lignin: Selective production of Vanillin," Applied Catalysis A General (2020) 598: 117567.

Rovio, S. et al. "Lignin oxidation mechanisms under oxygen delignification conditions. Part 2: Advanced methods for the detailed characterization of lignin oxidation mechanisms," Holzforschung (2011) 65:575.

Rude, A. and Schirmer, A. "New microbial fuels: a biotech perspective," Current Opinion in Microbiology (2009) 12:274-281.

Salmon, I. et al. "CO2 Capture by Alkaline Solution for Carbonate Production: A Comparison between a Packed Column and a Membrane Contactor," Appl. Sci. (2018) 8:996.

Schutyser, W. et al. "Revisiting alkaline aerobic lignin oxidation," Green Chem. (2018) 20:3828.

Si, B. et al. "Inhibitors degradation and microbial response during continuous anaerobic conversion of hydrothermal liquefaction wastewater," Science of the Total Environment (2018) 630:1124.

Suzuki, H. et al. "Wet oxidation of lignin model compounds and acetic acid production," J. Mater. Sci. (2006) 41:1591.

Thomsen, T. et al. "Low temperature circulating fluidized bed gasification and co-gasification of municipal sewage sludge. Part 1: Process performance and gas product characterization," Waste Management (2017) 66:123.

Thunman, H. et al. "Advanced biofuel production via gasification—lessons learned from 200 man-years of research activity with Chalmers' research gasifier and the GoBiGas demonstration plant," Energy Science and Engineering (2018) 6(1): 6-34.

Wang, G. et al. "Experimental and modeling studies on CO2 gasification of biomass chars," Energy (2016) 114:143.

Zhang, X. "Thermodynamic and economic analysis of biomass partial gasification process," Applied Thermal Engineering (2018) 129:410.

Zhang, Y. et al. "Exploration and practice to improve the kinetic analysis of char-0O2 gasification via thermogravimetric analysis," Chemical Engineering Journal (2019) 359:298.

The invention claimed is:

1. A method of processing lignin-rich process residual comprising the steps of:
providing a solution of at least 10 wt. % lignin-rich process residual dry matter in which Klason lignin content of the non-ash content of the residual is at least 60 wt. % dissolved in an aqueous solution of NaOH, KOH or other strong hydroxide base having pH at least 12 and molar ratio of hydroxide base:lignin residual at least 0.4;
subjecting the solution to alkaline oxidation at temperature >100° C. under applied oxygen partial pressure at least 3 bar for residence time sufficient to yield products that are water soluble at pH 7 comprising at least 50 wt. % of the amount of lignin residual dry matter dissolved in the solution before oxidation;
fractionating oxidation products produced during alkaline oxidation into lower and higher molecular weight components.

2. The method of claim 1 wherein the primary component of products from alkaline oxidation is carboxylic acids.

3. The method of claim 1 wherein the solution is subject to alkaline oxidation at temperature within the range 130 to 180° C. for a residence time within the range 15 to 60 minutes.

4. The method of claim 1 wherein the lignin-rich process residual is recovered from a biological conversion process.

5. The method of claim 1 wherein oxygen partial pressure is applied during alkaline oxidation during a heat up phase and during the first half of the reaction mixture's residence at tempera-ture within the range 130 to 180° C.

6. The method of claim 1 wherein oxygen partial pressure is applied during alkaline oxidation during the entire period of the reaction mixture's residence at temperature within the range 130 to 180° C. for a time between 15 and 60 minutes.

7. The method of claim 1 wherein fractionation is achieved using a ceramic or polymer ultrafil-tration membrane with a molecular weight cut-off <2 kD.

8. The method of claim 7 further characterized in that the pH of the resulting lower molecular weight fraction is adjusted to within the range 7 to 8.5 using $CO_2$.

9. The method of claim 1 further characterized in that the resulting lower molecular weight fraction with or without adjustment of pH is fed to anaerobic digestion to produce biomethane.

10. The method of claim 9 wherein anaerobic digestion is conducted using a fixed film digester.

11. The method of claim 10 wherein the digester is a fixed orientation fixed film digester.

12. The method of claim 1 further characterized in that the resulting lower molecular weight fraction of oxidation products is subject to treatment with $CO_2$ and acetone precipitation of carbonate salts is subsequently performed with the $CO_2$ treated lower molecular weight fraction.

13. The method of claim 1 wherein KOH is used in the aqueous solution subject to alkaline oxidation.

14. The method of claim 13 further characterized in that the resulting lower molecular weight fraction of oxidation products is subject to treatment with $CO_2$ and acetone precipitation of potassium carbonate is subsequently performed with the $CO_2$ treated lower molecular weight fraction.

15. The method of claim 1 further characterized in that excess process heat produced by the alkaline oxidation reaction is recovered and applied towards other processes.

16. The method of claim 15 wherein the other process to which excess process heat is applied is drying residual solids remaining after lignin recovery from anaerobic digestion of steam pretreated lignocellulosic feedstocks.

* * * * *